United States Patent
D'Mello et al.

(10) Patent No.: US 10,188,709 B2
(45) Date of Patent: Jan. 29, 2019

(54) COMPOSITIONS AND METHODS FOR THE TREATMENT OF PHENYLKETONURIA (PKU)

(71) Applicant: UNIVERSITY OF THE SCIENCES, Philadelphia, PA (US)

(72) Inventors: Anil P. D'Mello, Bryn Mawr, PA (US); Kush Patel, Gujarat (IN)

(73) Assignee: University of the Sciences, Philadelphia, PA (US)

( * ) Notice: Subject to any disclaimer, the term of this patent is extended or adjusted under 35 U.S.C. 154(b) by 0 days.

(21) Appl. No.: 15/495,410

(22) Filed: Apr. 24, 2017

(65) Prior Publication Data

US 2017/0304414 A1    Oct. 26, 2017

Related U.S. Application Data

(60) Provisional application No. 62/327,050, filed on Apr. 25, 2016.

(51) Int. Cl.
| | | |
|---|---|---|
| *A61K 38/51* | (2006.01) | |
| *A61K 9/50* | (2006.01) | |
| *A61K 9/16* | (2006.01) | |
| *A61K 38/42* | (2006.01) | |
| *A61K 9/00* | (2006.01) | |

(52) U.S. Cl.
CPC ............ *A61K 38/51* (2013.01); *A61K 9/0053* (2013.01); *A61K 9/1652* (2013.01); *A61K 9/1658* (2013.01); *A61K 9/5047* (2013.01); *A61K 9/5052* (2013.01); *A61K 38/42* (2013.01); *C12Y 403/01024* (2013.01)

(58) Field of Classification Search
CPC .... A61K 38/51; A61K 9/5052; A61K 9/5047; A61K 9/1658; A61K 9/1652; A61K 38/42; A61K 9/0053; C12Y 403/01024
See application file for complete search history.

(56) References Cited

U.S. PATENT DOCUMENTS

2016/0143961 A1*    5/2016  Berry ................... A61K 9/0031
                                                              424/93.3

OTHER PUBLICATIONS

Ahmad, et al., "Biocompatible and Mucoadhesive Bacterial Cellulose-g-Poly(acrylic acid) Hydrogels for Oral Protein Delivery," Mol. Pharmaceutics, vol. 11, Sep. 2014, pp. 4130-4142.
Anirudhan, et al., "Selective adsorption of hemoglobin using polymer-grafted-magnetite nanocellulose composite," Carbohydrate Polymers, vol. 93, Jan. 2013, pp. 518-527.
Arola, et al., "Immobilization-Stabilization of Proteins on Nanofibrillated Cellulose Derivatives and Their Bioactive Film Formation," Biomacromolecules, vol. 13, Jan. 2012, pp. 594-603.
Assaad, et al., "Polyelectrolyte Complex of Carboxymethyl Starch and Chitosan as Protein Carrier: Oral Administration of Ovalbumin," Journal of Biomaterials Science, Polymer Edition, vol. 23, No. 13, May 2012, pp. 1713-1728.

(Continued)

*Primary Examiner* — Trevor Love
(74) *Attorney, Agent, or Firm* — Saul Ewing Arnstein & Lehr LLP; Domingos J. Silva

(57) ABSTRACT

The present invention provides compositions for the treatment of phenylketonuria in mammals, as well as methods of preparing said compositions. The present invention also provides methods of treating phenylketonuria using the compositions of the invention.

19 Claims, 4 Drawing Sheets

L-Phenylalanine

*trans*-cinnamic acid

(56) References Cited

OTHER PUBLICATIONS

Boppana, et al., "Interpenetrating network hydrogel beads of carboxymethylcellulose and egg albumin for controlled release of lipid lowering drug," Journal of Microencapsulation, vol. 27(4), 2010, pp. 337-344.
Bourget, et al., "Effects of Oral Administration of Artificial Cells Immobilized Phenylalanine Ammonia-Lyase on Intestinal Amino Acids of Phenylketonuric Rats," Biomat, Art Cells, Art Org, vol. 17, No. 2, 1989, pp. 161-181.
Bourget, et al., "Phenylalanine ammonia-lyase immobilized in microcapsules for the depletion of phenylalanine in plasma in phenylketonuric rat model," Biochimica et Biophysica Acta, vol. 883, 1986, pp. 432-438.
Bourget, et al., "Phenylalanine ammonia-lyase immobilized in semipermeable microcapsules for enzyme replacement in phenylketonuria," FEBS Letters, vol. 180, No. 1, Jan. 1985, pp. 5-8.
Carlsson, et al., "Quantification of protein concentration by the Bradford method in the presence of pharmaceutical polymers," Analytical Biochemistry, vol. 411, 2011, pp. 116-121.
Chang, et al., "A New Theory of Enterorecirculation of Amino Acids and Its Use for Depleting Unwanted Amino Acids Using Oral Enzyme-Artificial Cells, as in Removing Phenylalanine in Phenylketonuria," Art Cells, Blood Subs and Immob Biotech, vol. 23, No. 1, 1995, pp. 1-21.
Chang, et al.,"Procedures for Microencapsulation of Enzymes, Cells and Genetically Engineered Microorganisms," Molecular Biotechnology, vol. 17, Issue 3, Mar. 2001, pp. 249-260.
Chang,T.M.S. et al., "Recycling of NAD(P) by Multienzyme Systems Immobilized by Microencapsulation in Artificial Cells," Methods in Enzymology, vol. 136, 1987, pp. 67-82.
Elversson, et al., "In situ coating—An approach for particle modification and encapsulation of proteins during spray-drying," Intl Journal of Pharmaceutics, vol. 323, Jun. 2006, pp. 52-63.
Everaert, et al., "Optimisation of HPMC ophthalmic inserts with sustained release properties as a carrier for thermolabile therapeutics," Intl Journal of Pharmaceutics, vol. 528, Jun. 2017, pp. 395-405.
Habibi-Moini, et al., "Evaluation of possible reasons for the low phenylalanine ammonia lyase activity in cellulose nitrate membrane microcapsules," Intl Journal of Pharmaceutics. vol. 215, 2001, pp. 185-196.
Katzhendler, et al., "Investigating the Structure and Properties of Hydrated Hydroxypropyl Methylcellulose and Egg Albumin Matrices Containing Carbamazepine: EPR and NMR Study," Pharmaceutical Research, vol. 17, No. 10, Jun. 2000, pp. 1299-1308.
Kindberg, et al., "Uptake and degradation of radioactively labelled albumin microspheres as markers for Kupffer cell phagocytosis," Cell Tissue Res, vol. 300, May 2000, pp. 397-400.
Muller, et al., "The Biopolymer Bacterial Nanocellulose as Drug Delivery System: Investigation of Drug Loading and Release using the Model Protein Albumin," J Pharmaceutical Sci, vol. 102, No. 2, Feb. 2013, pp. 579-592.
Okhamafe, et al., "Modulation of protein release from chitosan-alginate microcapsules using the pH-sensitive polymer hydroxypropyl methylcellulose acetate succinate," J Microencapsulation, vol. 13, No. 5, Jan. 1996, pp. 497-508.
Paukkonen, et al., "Nanofibrillar cellulose hydrogels and reconstructed hydrogels as matrices for controlled drug release, Intl Journal of Pharmaceutics," vol. 532, Sep. 2017, pp. 269-280.
Remunan-Lopez, et al., "Development of new chitosan-cellulose multicore microparticles for controlled drug delivery," European Journal of Pharmaceutics and Biopharmaceutics, vol. 45, 1998, pp. 49-56.
Salama, et al., "Carboxymethyl cellulose based hybrid material for sustained release releaseof protein drugs," Intl Journal of Biological Macromolecules, vol. 93, Apr. 2016, pp. 1647-1652.
Silva, et al., "Wound-healing evaluation of entrapped active agents into protein microspheres over cellulosic gauzes," Biotechnol J, vol. 8, 2013, pp. 1-10.
Singla, et al., "Sustained delivery of BSA/HSA from biocompatible plant cellulose nanocrystals for in vitro cholesterol release from endothelial cells," Intl Journal of Biological Macromolecules, vol. 104, Jun. 2017, pp. 748-757.
Song, et al., "Effect of net surface charge on physical properties of the cellulose nanoparticles and their efficacy for oral protein delivery," Carbohydrate Polymers, vol. 121, 2015, pp. 10-17.
Song, et al., "Preparation and Characterization of Novel Quaternized Cellulose Nanoparticles as Protein Carriers," Macromol Biosci. vol. 9, 2009, pp. 857-863.
Soudry-Kochavi, et al., "Improved oral absorption of exenatide using an original nanoencapsulation and microencapsulation approach," J Controlled Rel, vol. 217, Sep. 2015, pp. 202-210.
Tabata, et al., "Neovascularization effect of biodegradable gelatin microspheres incorporating basic fibroblast growth factor," J Biomater Sci Polymer Edn, vol. 10, No. 1, 1999, pp. 79-94.

* cited by examiner

L-Phenylalanine        trans-cinnamic acid

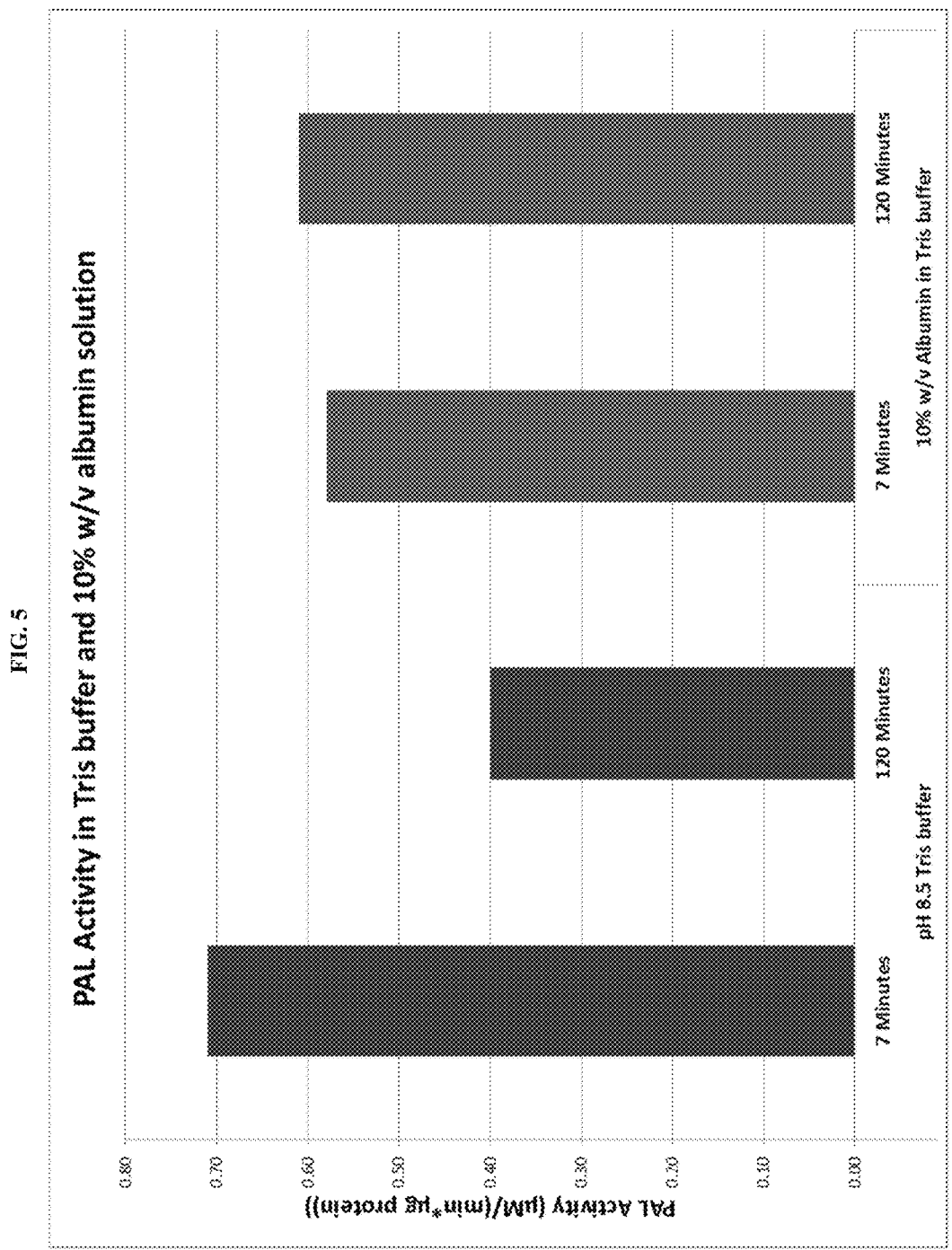

COMPOSITIONS AND METHODS FOR THE TREATMENT OF PHENYLKETONURIA (PKU)

CROSS REFERENCE TO RELATED APPLICATIONS

The present application is entitled to priority under 35 U.S.C. § 119(e) to U.S. Provisional Application No. 62/327,050, filed Apr. 25, 2016, which application is hereby incorporated by reference herein in its entirety.

BACKGROUND OF THE INVENTION

Phenylketonuria (PKU) is an inborn error of metabolism, which is characterized by marked reduction or complete absence of the activity of the phenylalanine hydroxylase (PAH) enzyme. In normal subjects, PAH catalyzes the conversion of L-phenylalanine (L-Phe) to L-tyrosine (L-Tyr). Loss of function of PAH in PKU patients results in dramatic accumulation of L-Phe in their blood and brain. L-Phe is neurotoxic at high concentrations and causes irreversible impairment of cognitive development in the PKU-afflicted subject.

In mammals, L-Phe is an essential amino acid that is not produced by the body and is derived solely from diet. The current therapy for PKU is a low-L-Phe-content synthetic diet that limits dietary L-Phe intake to less than 500 mg/day. Screening tests in newborns enables early identification of PKU and allows dietary treatment to begin before neurological damage occurs. Current guidelines require diet therapy to be continued for a lifetime. Unfortunately, the diet has unsatisfactory organoleptic properties that reduces compliance, especially in adolescents and adults, which may lead to impaired neurophysiological function. In pregnant PKU mothers, non-compliance results in increased fetal exposure to L-Phe, which is associated with a dramatic increase in fetal abnormalities. As another complication, the low-L-Phe-content synthetic diet is deficient in several nutrients, and may cause growth retardation, osteoporosis and even brain development problems. Failure to properly treat PKU patients may irreversibly compromise their full neurodevelopmental potential.

Alternative PKU therapies have been explored, such as gene therapy, but none of these strategies have led to a permanent correction of PAH activity. Gene therapy methods initially yield improved results, but patients eventually develop an immune response against the therapeutic vectors, leading to therapy rejection.

There is thus a need in the art for methods of treating PKU-afflicted patients. Such methods should avoid the drawbacks of the low-L-Phe-content diet and gene therapy based treatments. The present invention addresses this need.

BRIEF SUMMARY OF THE INVENTION

The invention provides a pharmaceutical composition comprising a microcapsule, which is enveloped by a membrane comprising ethyl cellulose. The invention further provides a method of preparing the compositions of the invention. The invention further provides a method of treating phenylketonuria in a subject in need thereof.

In certain embodiments, the microcapsule comprises in its interior phenylalanine ammonia lyase and at least one selected from the group consisting of hemoglobin and fatty acid-free albumin.

In certain embodiments, the microcapsule further comprises in its interior a carrier compound. In other embodiments, the carrier compound is at least one selected from the group consisting of polyvinylalcohol, polysorbate 80, bovine serum albumin, a magnesium salt, a manganese salt, and glycerol.

In certain embodiments, L-phenylalanine flows freely across the membrane, and wherein a polypeptide with a molecular weight greater than about 20 kD cannot significantly cross the membrane. In other embodiments, the membrane is not chemically or physically degraded or digested within the gastrointestinal tract of a human.

In certain embodiments, the microcapsule has a diameter ranging from about 1 µm to about 10 µm. In other embodiments, the microcapsule has a diameter ranging from about 3 to about 5 µm.

In certain embodiments, the method of preparing a composition of the invention comprises contacting ethyl cellulose with dichloromethane to form an organic phase. In other embodiments, the method of preparing a composition of the invention comprises contacting phenylalanine ammonia lyase, at least one selected from the group consisting of hemoglobin and fatty acid-free albumin, buffered water solution, and optionally a carrier compound, thus forming an aqueous phase. In yet other embodiments, the method of preparing a composition of the invention comprises contacting the aqueous phase with the organic phase to form a system. In yet other embodiments, the method of preparing a composition of the invention comprises sonicating the system to form an emulsion. In yet other embodiments, the method of preparing a composition of the invention comprises spray drying the emulsion to yield the composition.

In certain embodiments, the organic phase comprises about 2-6% (w/v) ethyl cellulose. In other embodiments, the aqueous phase comprises about 5-15% (w/v) of one selected from the group consisting of hemoglobin, fatty acid-free albumin, and a mixture of hemoglobin and fatty acid-free albumin. In yet other embodiments, the aqueous phase comprises about 5-15% (w/v) phenylalanine ammonia lyase.

In certain embodiments, the method comprises administering to the subject a therapeutically effective amount of at least one composition of the invention. In other embodiments, the composition is administered to the subject orally. In yet other embodiments, the composition is administered at a time selected from before mealtime, during mealtime, and after mealtime. In yet other embodiments, administration of the composition to the subject prevents increase, amelioratse, or reduce phenylalanine levels in the blood of the subject. In yet other embodiments, administration of the composition to the subject treats, ameliorates or prevents at least one symptom of phenylketonuria in the subject. In yet other embodiments, the at least one symptom is selected from the group consisting of seizures, tremors, shaking, stunted growth, hyperactivity, eczema, musty odor, mental deficits, behavioral disorders and skin discoloration. In yet other embodiments, the subject is a mammal. In yet other embodiments, the subject is human.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 5 is a bar graph illustrating certain effects of fatty acid-free albumin on the magnitude of trans-cinnamic acid mediated product inhibition of phenylalanine ammonia lyase.

DETAILED DESCRIPTION OF THE INVENTION

Figure 1:
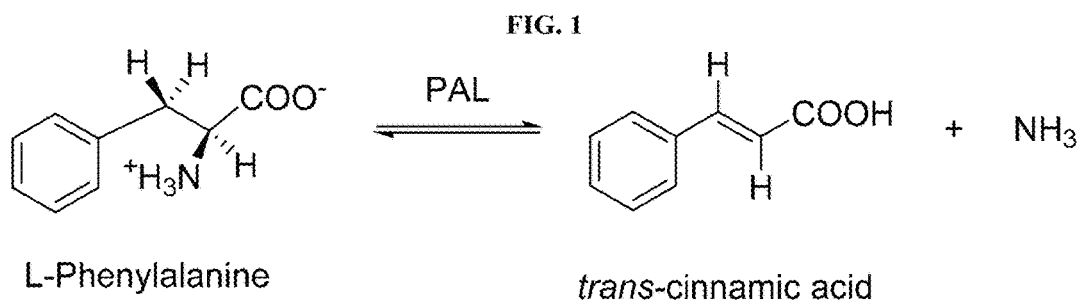
FIG. 1 is a reaction scheme illustrating the phenylalanine ammonia lyase (PAL)-catalyzed conversion of L-phenylalanine (L-Phe) to trans-cinnamic acid (TCA) and ammonia.
Figure 2:
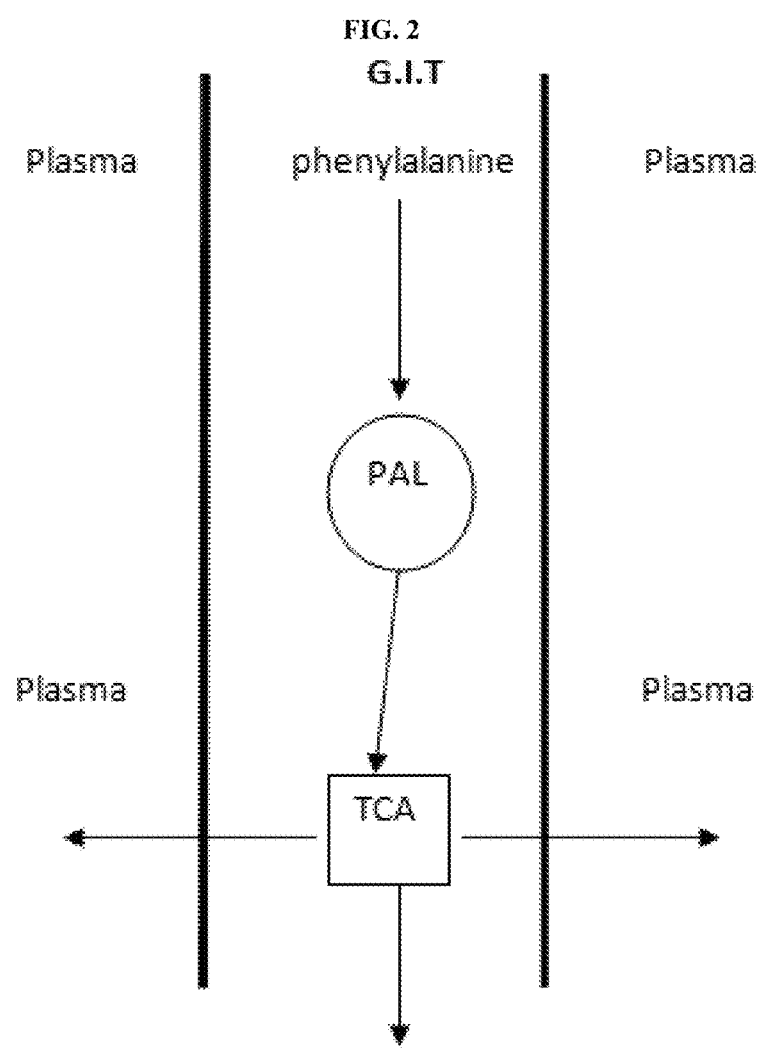
FIG. 2 is a non-limiting schematic representation of microcapsules of the invention. Microcapsules, represented by the circle labeled "PAL", are ingested into the gastrointestinal tract (G.I.T.). Without wishing to be limited by any theory, while in the G.I.T., L-Phe enters the microcapsules and is converted into TCA, which can then safely enter the plasma and be further metabolized by the body.

The invention relates in certain aspects to the unexpected discovery that microcapsules containing phenylalanine ammonia lyase (PAL) and at least one selected from the group consisting of hemoglobin (Hb) and fatty acid-free albumin can be used to treat phenylketonuria-afflicted subjects. In certain embodiments, the microcapsule comprises in its interior fatty acid-free albumin. In other embodiments, the microcapsule comprises in its interior Hb. In yet other embodiments, the microcapsule comprises in its interior a mixture of fatty acid-free albumin and Hb. In yet other embodiments, the microcapsule further comprises in its interior a carrier compound. In yet other embodiments, the membrane comprises ethyl cellulose. In yet other embodiments, the microcapsule membrane is semi-permeable, allowing the free passage of L-phenylalanine in and out of the microcapsule (i.e., across the microcapsule membrane) but preventing the passage of polypeptides in and out of the microcapsule. In yet other embodiments, the microcapsule membrane is essentially impermeable to polypeptides with a molecular weight greater than about 20 kD. In yet other embodiments, the microcapsule membrane is not degraded or digested by the gastrointestinal tract of a human.

The invention relates in other aspects to methods of preparing ethyl cellulose microcapsules containing PAL, optionally a carrier compound, and at least one selected from the group consisting of Hb and fatty acid-free albumin.

The invention also relates to methods of treating phenylketonuria in an afflicted subject. In certain embodiments, the methods of the invention prevent the increase, or reduce, the L-Phe level in the blood of the subject. In other embodiments, the methods of the invention treat, ameliorate and/or prevent one or more symptoms of phenylketonuria.

Without wishing to be limited by any theory, microcapsules of the invention allow PAL contained therein to remain active in the gastro-intestinal tract of a subject by protecting, or minimizing, physical and/or chemical degradation of the enzyme. Catalytically active PAL catalyzes the conversion of L-Phe to TCA. While subjects suffering from PKU cannot metabolize L-Phe, TCA is a non-toxic metabolite that can be eliminated as hippurate, cinnamic acid and benzoic acid in the urine.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described. As used herein, each of the following terms has the meaning associated with it in this section.

Generally, the nomenclature used herein and the laboratory procedures in cell culture, molecular genetics, pharmacology, food science and organic chemistry are those well-known and commonly employed in the art.

Standard techniques are used for biochemical and/or biological manipulations. The techniques and procedures are generally performed according to conventional methods in the art and various general references (e.g., Sambrook and Russell, 2012, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the terms "analog," "analogue," or "derivative" are meant to refer to a chemical compound or molecule prepared from another compound or molecule by one or more chemical reactions. As such, an analog can be a structure similar to, or based on, the structure of any small molecule inhibitor described herein, and/or may have a similar or dissimilar metabolic behavior.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "essentially impermeable" as applied to a membrane regarding a certain molecule indicates that the molecule does not cross the membrane, or crosses the membrane at such low rates that the amount of molecule crossing the membrane cannot be detected, is below detection level, and/or has no significant physiological effect. In certain embodiments, an essentially impermeable membrane comprises an impermeable membrane.

As used herein, the term "fatty acid-free albumin" refers to albumin that comprises less than about 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002% or 0.001% fatty acid.

The phrase "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

As used herein, the term "pharmaceutical composition" or "composition" refers to a mixture of at least one compound and/or composition useful within the invention with a pharmaceutically acceptable carrier. The pharmaceutical composition facilitates administration of the compound and/or composition to a subject.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound and/or composition useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound and/or composition useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound and/or composition useful within the invention, and are physiologically acceptable to the patient. Supplementary active compounds may also be incorporated into the compositions. The "pharmaceutically acceptable carrier" may further include a pharmaceutically acceptable salt of the compound and/or composition useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compound and/or composition prepared from pharmaceutically acceptable non-toxic acids and bases, including inorganic acids, inorganic bases, organic acids, inorganic bases, solvates, hydrates, and clathrates thereof. Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable pharmaceutically acceptable base addition salts of compounds and/or compositions of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound and/or composition by reacting, for example, the appropriate acid or base with the compound and/or composition.

The terms "pharmaceutically effective amount" and "effective amount" refer to a nontoxic but sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation. By "pharmaceutical formulation" it is further meant that the carrier, solvent, excipient(s) and/or salt must be compatible with the active ingredient of the formulation (e.g., a compound of the invention). It is understood by those of ordinary skill in this art that the terms "pharmaceutical formulation" and "pharmaceutical composition" are generally interchangeable, and they are so used for the purposes of this application.

As used herein, the term "prevent," "prevention," or "preventing" refers to any method to partially or completely prevent or delay the onset of one or more symptoms or features of a disease, disorder, and/or condition. Prevention is causing the clinical symptoms of the disease state not to develop, i.e., inhibiting the onset of disease, in a subject that may be exposed to or predisposed to the disease state, but does not yet experience or display symptoms of the disease state. Prevention may be administered to a subject who does not exhibit signs of a disease, disorder, and/or condition.

As used herein, the term "subject," "patient" or "individual" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

As used herein, the term "therapeutically effective amount" is an amount of a compound and/or composition of the invention, that when administered to a patient, treats, minimizes and/or ameliorates a symptom of the disease or disorder. The amount of a compound and/or composition of the invention that constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

The terms "treat," "treating," and "treatment," refer to therapeutic or preventative measures described herein. The methods of "treatment" employ administration to a subject, in need of such treatment, a compound and/or composition of the present invention, for example, a subject afflicted a disease or disorder, or a subject who ultimately may acquire such a disease or disorder, in order to prevent, cure, delay, reduce the severity of, or ameliorate one or more symptoms of the disorder or recurring disorder, or in order to prolong the survival of a subject beyond that expected in the absence of such treatment.

The following abbreviations are used herein: BSA, bovine serum albumin; DCM, dichloromethane; G.I.T., gastrointestinal tract; Hb, hemoglobin; L-Phe, L-phenylalanine; PAH, phenylalanine hydroxylase; PAL, phenylalanine lyase; Phe, phenylalanine; PKU, phenylketonuria; rAAV, recombinant adeno-associated virus; RP-HPLC, reverse phase high performance liquid chromatography; TCA, trans-cinnamic acid; Tris, tris(hydroxymethyl) aminomethane; w/o, water-in-oil emulsion.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds and/or Compositions

The present invention includes a microcapsule which membrane comprises ethyl cellulose, wherein a pharmaceutical composition comprising phenylalanine ammonia lyase (PAL) and at least one selected from the group consisting of Hb and fatty acid-free albumin is encapsulated within the membrane.

In certain embodiments, the microcapsule comprises in its interior fatty acid-free albumin. In other embodiments, the microcapsule does not comprise in its interior fatty acid-free albumin. In yet other embodiments, the microcapsule comprise in its interior Hb. In yet other embodiments, the microcapsule does not comprise in its interior Hb. In yet other embodiments, the microcapsule comprises in its interior a mixture of fatty acid-free albumin and Hb. In yet other embodiments, the fatty acid-free albumin is bovine. In yet other embodiments, the fatty acid-free albumin is human. In yet other embodiments, the fatty acid-free albumin is recombinant human.

In certain embodiments, the microcapsule comprises in its interior a carrier compound. In other embodiments, the microcapsule does not comprise in its interior a carrier compound. In a non-limiting aspect, the carrier compound helps preserve PAL activity upon storage of the microcapsules as spray dried microcapsules. In a non-limiting aspect, upon oral administration of the microcapsules, the carrier compound helps create an environment within the microcapsule that protects encapsulated PAL from degradation in the gastrointestinal tract. In a non-limiting aspect, the carrier compound helps maximize (and/or helps prevent loss of) catalytic activity of the encapsulated PAL. In yet other embodiments, the carrier compound is one or more selected from the group consisting of polyvinylalcohol, polysorbate 80, bovine serum albumin, a magnesium salt, a manganese salt, and glycerol.

In certain embodiments, the microcapsule membrane is a semi-permeable membrane. In other embodiments, the membrane allows free passage of L-Phe in and out of the microcapsule (i.e., across the microcapsule membrane) but prevent passage of polypeptides in and out of the microcapsule. In other embodiments, the microcapsule membrane is essentially impermeable to polypeptides with a molecular weight greater than about 20 kD. In yet other embodiments, the microcapsule membrane is impermeable to trypsin. In yet other embodiments, the membrane is not significantly physically and/or chemically degraded or digested within the human gastrointestinal tract.

In certain embodiments, the diameter of the microcapsule ranges from about 1 µm to about 10 µm. In other embodiments, the diameter of the microcapsule is about 5 µm. In other embodiments, the diameter of the microcapsule is about 3 µm. In other embodiments, the diameter of the microcapsule ranges from about 3 to about 5 µm, about 3 to about 4 µm, or about 4 to about 5 µm.

Compounds described herein also include isotopically labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$ and $^{35}S$. In Certain embodiments, substitution with heavier isotopes such as deuterium affords greater chemical stability. Isotopically labeled compounds are prepared by any suitable method or by processes using an appropriate isotopically labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

The present invention further provides pharmaceutical compositions. The pharmaceutical compositions described herein may be prepared by any method known or hereafter developed in the art of pharmacology. In general, such preparatory methods include bringing the active ingredient into association with a carrier or one or more other accessory ingredients, and then, if necessary or desirable, shaping or packaging the product into a desired single- or multi-dose unit.

Salts

The compounds and/or compositions described herein may form salts with acids and/or bases, and such salts are included in the present invention. In certain embodiments, the salts are pharmaceutically acceptable salts. The term "salts" embraces addition salts of free acids and/or basis that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds and/or compositions useful within the methods of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds and/or compositions of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (also known as N-methylglucamine) and procaine. All of these salts may be prepared from the corresponding compound by reacting, for example, the appropriate acid or base with the compound and/or composition.

Methods of Preparing

The present invention includes methods of preparing microcapsules of the invention. In certain embodiments, the microcapsule comprises a membrane comprising ethyl cellulose. In other embodiments, the microcapsule comprises in its interior a pharmaceutical composition comprising phenylalanine ammonia lyase (PAL) and at least one selected from the group consisting of Hb and fatty acid-free albumin encapsulated therewithin. In yet other embodiments, the microcapsule further comprises in its interior a carrier compound.

In certain embodiments, the method comprises contacting ethyl cellulose with dichloromethane to form an organic phase. In other embodiments, the method comprises contacting Hb and/or fatty acid-free albumin, PAL, optionally a carrier compound, and a buffered water solution to form an aqueous phase. In yet other embodiments, the method comprises contacting the aqueous phase with the organic phase to form a system. In yet other embodiments, the method comprises sonicating the system to form an emulsion. In yet other embodiments, the method comprises spray drying the emulsion.

In certain embodiments, the organic phase comprises about 4% (w/v) ethyl cellulose. In other embodiments, the organic phase comprises about 2-6% (w/v) ethyl cellulose. In yet other embodiments, the organic phase comprises about 2-3% (w/v), 3-4% (w/v), 4-5% (w/v), and/or 5-6% (w/v) ethyl cellulose.

In certain embodiments, the aqueous phase comprises about 10% (w/v) Hb. In other embodiments, the aqueous phase comprises about 10% (w/v) fatty acid-free albumin. In yet other embodiments, the aqueous phase comprises about 10% (w/v) mixture of Hb and fatty acid-free albumin. In yet other embodiments, the aqueous phase comprises about 5-15% (w/v) Hb or fatty acid-free albumin. In yet other embodiments, the aqueous phase comprises about 5-6% (w/v), 6-7% (w/v), 7-8% (w/v), 8-9% (w/v), 9-10% (w/v), 10-11% (w/v), 11-12% (w/v), 12-13% (w/v), 13-14% (w/v), and/or 14-15% (w/v) of Hb or fatty acid-free albumin. In yet other embodiments, the aqueous phase comprises about 5-15% (w/v) mixture of Hb and fatty acid-free albumin. In yet other embodiments, the aqueous phase comprises about 5-6% (w/v), 6-7% (w/v), 7-8% (w/v), 8-9% (w/v), 9-10% (w/v), 10-11% (w/v), 11-12% (w/v), 12-13% (w/v), 13-14% (w/v), and/or 14-15% (w/v) mixture of Hb and fatty acid-free albumin.

In certain embodiments, the aqueous phase comprises from about 5-15% (w/v) PAL. In other embodiments, the aqueous phase comprises about 5%, 6%, 7%, 8%, 9%, 10%, 11%, 12%, 13%, 14%, or 15% (w/v) PAL. In yet other embodiments, the aqueous phase comprises about 5-6%, 6-7%, 7-8%, 8-9%, 9-10%, 10-11%, 11-12%, 12-13%, 13-14%, and/or 14-15% (w/v) PAL.

In certain embodiments the buffered water solution comprises tris(hydroxymethyl) aminomethane. In other embodiments, the aqueous phase is buffered to a pH of about 8.5.

In certain embodiments, the carrier compound is absent from the composition. In other embodiments, the carrier compound is present in the composition. In yet other embodiments, the carrier compound is one or more selected from the group consisting of polyvinylalcohol, polysorbate 80, bovine serum albumin, a magnesium salt, a manganese salt, and glycerol.

Methods of Treating

The present invention includes methods of treating phenylketonuria in a subject in need thereof. The method comprises administering to the subject a therapeutically effective amount of a microcapsule of the invention. In certain embodiments, the microcapsule comprises a membrane comprising ethyl cellulose. In other embodiments, the microcapsule comprises in its interior a pharmaceutical composition comprising PAL and at least one selected from the group consisting of Hb and fatty acid-free albumin encapsulated therewithin.

In certain embodiments, the microcapsule membrane is a semi-permeable membrane. In other embodiments, the membrane allows free passage of L-Phe in and out of the microcapsule (i.e., across the microcapsule membrane) but preventing passage of polypeptides in and out of the microcapsule. In other embodiments, the microcapsule membrane is essentially impermeable to polypeptides with a molecular weight greater than about 20 kD. In yet other embodiments, the microcapsule membrane is essentially impermeable to trypsin. In yet other embodiments the membrane is not significantly physically and/or chemically degraded or digested within the human gastrointestinal tract.

In other embodiments, the diameter of the microcapsule is about 1 μm, about 2 μm, about 3 μm, about 4 μm or about 5 μm.

In certain embodiments, the microcapsule is part of a pharmaceutical formulation further comprising at least a pharmaceutically acceptable carrier.

In certain embodiments, the administration of the microcapsule lowers, or prevents or ameliorates the increase of, L-Phe level in the blood of the subject. In other embodiments, the administration of the composition treats or prevents at least one symptom of phenylketonuria. In yet other embodiments, the at least one symptom is selected from the group consisting of seizures, tremors, shaking, stunted growth, hyperactivity, eczema, musty odor, mental deficits, behavioral disorders and skin discoloration.

In certain embodiments, the composition is administered to the subject orally.

In certain embodiments, a non-limiting example of an effective dose range for a therapeutic compound of the invention is from about 1 and 5,000 mg/kg of body weight/day.

In certain embodiments, the composition is administered at a time selected from before mealtime, during mealtime and after mealtime. In other embodiments, the composition is administered from about once a day to about ten times a day. In yet other embodiments, the composition is only administered when the subject has consumed food containing or thought of containing L-Phe. In yet other embodiments, the composition is administered orally to a subject suffering from PKU before a meal, along with a meal, or shortly after a meal.

In certain embodiments, the subject is a mammal. In other embodiments, the subject is human.

Administration/Dosage/Formulations

The regimen of administration may affect what constitutes an effective amount. The therapeutic formulations may be administered orally before a meal, during a meal, or after a meal. The therapeutic formulations may be administered to the subject either prior to or after the onset of a disease or disorder contemplated in the invention. Further, several divided dosages, as well as staggered dosages may be administered daily or sequentially. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/day.

One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular composition employed, the time of administration, the rate of excretion of the composition, the duration of the treatment, other drugs, compounds or materials used in combination with the composition, the age, sex, weight, condition, general health and prior medical history of the patient being treated, and like factors well known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is advantageous to formulate the compound and/or composition in dosage unit form for ease of administration and uniformity of dosage. Dosage unit form as used herein refers to physically discrete units suited as unitary dosages for the patients to be treated; each unit containing a predetermined quantity of therapeutic compound and/or composition calculated to produce the desired therapeutic effect in association with the required pharmaceutical vehicle. The dosage unit forms of the invention are dictated by and directly dependent on (a) the unique characteristics of the therapeutic compound and/or composition and the particular therapeutic effect to be achieved, and (b) the limitations inherent in the art of compounding/formulating such a therapeutic compound and/or composition for the treatment of a disease or disorder contemplated in the invention.

In certain embodiments, the compositions of the invention are formulated using one or more pharmaceutically acceptable excipients or carriers. In other embodiments, the pharmaceutical compositions of the invention comprise a therapeutically effective amount of a compound of the invention and a pharmaceutically acceptable carrier. In yet other embodiments, the compound of the invention is the only biologically active agent (i.e., capable of treating phenylketonuria) in the composition. In yet other embodiments, the compound of the invention is the only biologically active agent (i.e., capable of treating phenylketonuria) in therapeutically effective amounts in the composition.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions of the invention are administered to the patient in dosages that range from one to five times per day or more. In other embodiments, the compositions of the invention are administered to the patient in range of dosages that include, but are not limited to, once every day, every two days, every three days to once a week, and once every two weeks. In yet other embodiments, the compositions of the invention are administered before, along with, or after meals. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds and/or compositions of the invention for administration may be in the range of from about 1 μg to about 10,000 mg, about 20 μg to about 9,500 mg, about 40 μg to about 9,000 mg, about 75 μg to about 8,500 mg, about 150 μg to about 7,500 mg, about 200 μg to about 7,000 mg, about 3050 μg to about 6,000 mg, about 500 μg to about 5,000 mg, about 750 μg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments there between.

In some embodiments, the dose of a compound and/or composition of the invention is from about 1 mg and about 2,500 mg. In some embodiments, a dose of a compound and/or composition of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound and/or composition of the invention, alone or in combination with a second pharmaceutical agent; and instructions for using the compound to treat, prevent, or reduce one or more symptoms of a disease or disorder contemplated in the invention.

Formulations may be employed in admixtures with conventional excipients, i.e., pharmaceutically acceptable organic or inorganic carrier substances suitable for intraperitoneal, oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents.

Routes of administration of any of the compositions of the invention include intra-peritoneal, oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-peritoneal, intra-arterial, intravenous, intrabronchial, inhalation, and topical administration. Preferentially, the compound is formulated for oral administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethyl cellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation". For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e., having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e., drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of a disease or disorder contemplated in the invention. Using a wax/pH-sensitive polymer mix, a gastric insoluble composition may be obtained in which the active ingredient is entrapped, ensuring its delayed release.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds and/or compositions may be formulated with a suitable polymer or hydrophobic material that provides sustained release properties to the compounds and/or compositions. As such, the compounds and/or compositions useful within the methods of the invention may be administered in the form of microparticles, for example by injection, or in the form of wafers or discs by implantation.

In certain embodiments, the compounds and/or compositions of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, about 10 minutes, or about 1 minute and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, about 10 minutes, or about 1 minute and any and all whole or partial increments thereof after drug administration.

Dosing

The therapeutically effective amount or dose of a compound and/or composition of the present invention depends on the age and weight of the patient, the current medical condition of the patient and the progression of a disease or disorder contemplated in the invention. The skilled artisan is able to determine appropriate dosages depending on these and other factors.

A suitable dose of a compound and/or composition of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 5 or more times per day. When multiple dosages are used, the amount of each dosage may be the same or different. For example, a dose of 1 mg per day may be administered as two 0.5 mg doses, with about a 12-hour interval between doses.

It is understood that the amount of compound and/or composition dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the compound and/or composition of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In certain embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 5 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Trans-cinnamic acid, L-phenylalanine, triglyceride reagent A, glycerol, phenylalanine ammonia lyase, collodion, n-butyl benzoate and hemoglobin were obtained from Sigma Aldrich (St. Louis, Mo.). Ethyl cellulose was obtained from Dow chemical company (100 cps grade). Hemoglobin reagent set was obtained from Pointe Scientific. Bio-Rad protein dye reagent concentrate, 2-mercaptoethanol and Bradford's protein dye were obtained from Bio-Rad (Hercules, Calif.). Centricon tubes were obtained from Amicon (Beverly, Mass., USA). Trichloro acetic acid was acquired from Fischer.

Preparation of PAL from Glycerol Solution

Purified PAL was prepared from commercial 60% (v/v) solutions in glycerol. 0.48 mL of the 60% (v/v) solution were diluted to 1.5 mL using cold aqueous Tris buffer (pH 8.5). The diluted enzyme solution was split into 3 Centricon tubes each containing 0.5 mL, and centrifuged at 4° C. for 30 minutes and 1000*g. The filtrate from all 3 tubes was collected. This process was repeated two more times. The filtrate from all the washings was combined and weighed. The density was determined, and the volume was calculated. The filtrate (which contained the purified PAL) from all 3 tubes was combined, and diluted to 2 mL using cold Tris buffer. The diluted enzyme solution was divided into 200 µL aliquots and stored at −80° C.

Protein Quantification Using the Bradford's Assay

Bio-Rad protein reagent was used to quantify the amount of protein in a sample. Bovine serum albumin standards were prepared in the range of 2-10 µg amounts in deionized water. 800 µL of the albumin standard were then added to 200 µL of the protein reagent. The mixture was vortexed and incubated for 5 minutes. The absorbance was measured at a wavelength of 595 nm in a Shimadzu UV-1601 spectrophotometer. Standards were prepared in duplicates. The sample processing was as follows: a 15 µL aliquot of the sample solution was diluted to 30 µL. Ten microliters of this diluted sample were further diluted to 800 µL with deionized water. The 800 µL sample solution was incubated with 200 µL of the Bradford's reagent, and the absorbance of the complex was read. Protein content of the sample was then determined through comparison with the bovine serum albumin standards.

Reverse Phase—HPLC of Trans-Cinnamic Acid

Trans-cinnamic acid (TCA) is the product formed as a result of a PAL catalyzed conversion of Phe, which is the substrate. The RP-HPLC conditions are described in Table 1. A 1.5 mM stock solution of TCA was prepared using a methanol:Tris buffer (40:60) solution. This stock solution was used to prepare TCA standards ranging from 4.5 µM-67.5 µM in Tris buffer pH 8.5. Standards were prepared in duplicates on each day.

TABLE 1

| RP-HPLC parameters for TCA quantification | |
|---|---|
| Mobile Phase | 50 mM Phosphate buffer (pH 6.5):Methanol (92:8) |
| Column | Waters, Nova Pak, RP-C18 (3.9 × 150 mm) |
| Column Temperature | 40° C. |
| Flow rate | 1.0 mL/min |
| Detection | 270 nm |
| Injection volume | 25 µL |
| Run time | 13 mins |

Method to Determine the $V_{max}$ of Free PAL

A 20 µL (4.64 µg of protein) aliquot of glycerol free PAL was incubated with 380 µL of a 1500 µM Phe solution in Tris buffer pH 8.5 at 37° C. while stirring. The enzymatic reaction was stopped after 1, 3, 5, 7, 20 and 30 minutes by adding a 300 µL solution of trichloroacetic acid (10% w/v) solution to 100 µL of the reaction mixture and vortexing the resulting solution. The amount of TCA formed was determined using the HPLC technique with parameters listed in Table 1. Standards were treated similar to the samples.

Colorimetric Assay for Determination of Hemoglobin Concentration

Hemoglobin solution was prepared by adding 3 g of hemoglobin in 15 mL of cold Tris buffer pH 8.5. The suspension was stirred for 2 hours at 4° C. This suspension was then filtered through a Whatmann no. 42 filter. The concentration of hemoglobin in the filtrate was measured using a Drabkin's assay. 50 µL of the filtrate were diluted to 100 µL using Tris buffer. 10 µL of the dilution were added to 2 mL of hemoglobin reagent. The conversion of hemoglobin to cyanmethemoglobin was measured at 545 nm in a Shimadzu UV-1601 spectrophotometer. Standards obtained from Pointe Scientific were prepared in a concentration range of 1.14-11.4 g/dL and similarly processed.

Example 1: Preparation of Blank Microspheres 2 grams of ethyl cellulose powder were dissolved in 35 mL of dichloromethane. Additional dichloromethane was added to the solution until the final solution volume was 50 mL, yielding a 4% (w/v) solution of ethyl cellulose in dichloromethane. The solution was stirred for 2 hours to ensure complete dissolution. After dissolution, the resulting solution is then spray dried under the conditions described in Table 2. The product yield over two trials was found to be 71% and 69%.

TABLE 2

Conditions for spray drying ethyl cellulose in dichloromethane

| Polymer | Ethylcellulose (100 cps) |
|---|---|
| Pump rate | 25% |
| Inlet temperature | 40° C. |
| Outlet temperature | 35° C. |
| Aspirator | 100% |
| Feed concentration | 4% (w/v) |

Example 2: Microencapsulation of Hemoglobin by Spray Drying

A saturated solution of hemoglobin was prepared by dissolving 3 g of lyophilized bovine hemoglobin in 15 mL of Tris buffer pH 8.5. The solution was stirred at 4° C. for a period of 2 hours. The Hb solution was filtered through a Whatman no. 42 filter paper. The final concentration of the hemoglobin solution was determined to be 13% (w/v) Hb by Drabkin's assay. A 4% (w/v) ethyl cellulose solution was prepared by dissolving 2 g of ethyl cellulose in 35 mL of dichloromethane, and then adding dichloromethane until the final solution volume was 50 mL. 500 µL of the 13% (w/v) hemoglobin solution were added to 50 mL of the 4% (w/v) ethyl cellulose in dichloromethane. The Hb was then dispersed in the ethyl cellulose solution using a probe sonicator. The water-in-oil emulsion is then spray dried using the conditions described in Table 2. The product yield of this procedure was about 69%.

Example 3: Scanning Electron Microscopy of Microcapsules

Figure 3:
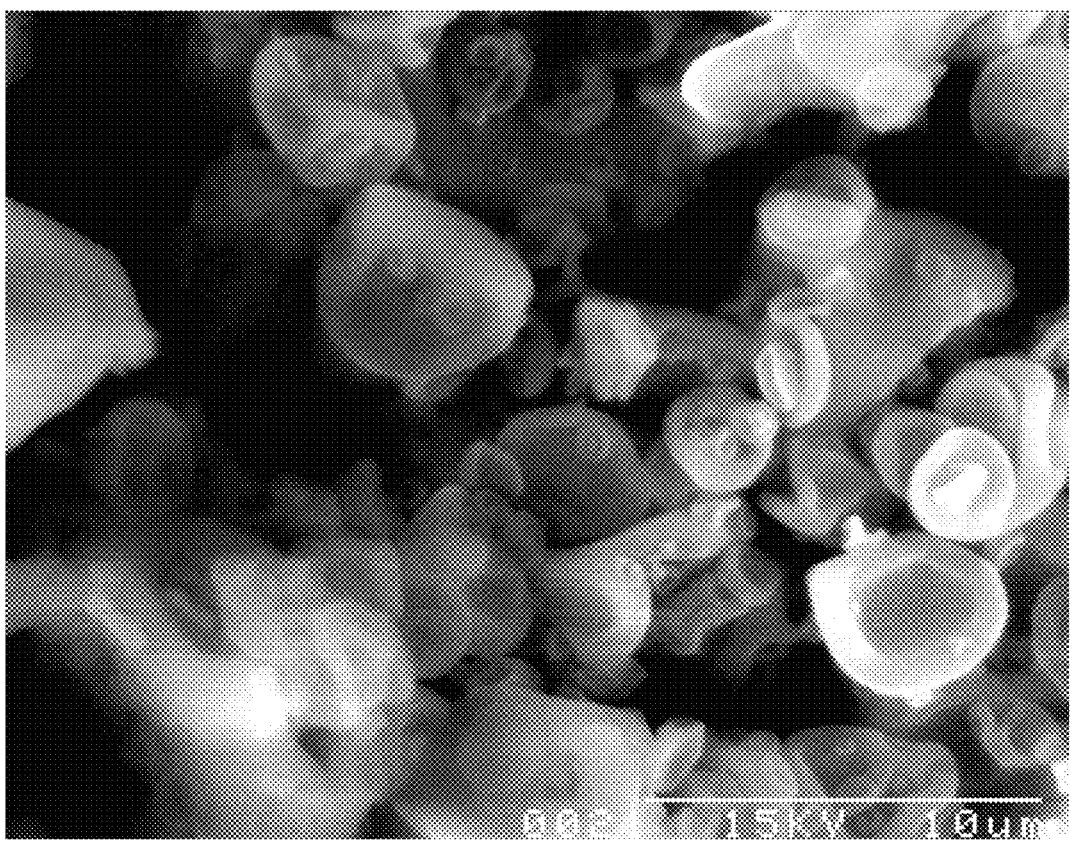
FIG. 3 is a scanning electron microscopy image of spray dried microcapsules of ethyl cellulose prepared through certain methods of the invention.

The microcapsules were initially mounted on aluminum stubs (Hitachi S-450 obtained from Electron Microscopy Sciences—Hartfield, Pa.) containing ultra-smooth carbon double sided adhesive tabs (Electron Microscopy Sciences—Hartfield, Pa.). The microcapsules were sputter coated with gold in an argon environment with minimum thickness using a Denton vacuum desk V sputter coater. The morphology of the microcapsules was studied using a Hitachi S-530 Scanning Electron Microscope (SEM). The photographs (FIG. 3) were taken at a beam intensity of 15 kV.

Example 4: Preparation of PAL/Hb Microcapsules 2 g of ethyl cellulose were dissolved in 50 ml of DCM to give a 4% (w/v) ethyl cellulose solution. A 150 µL aliquot of glycerol free PAL (0.64 mg/ml) was added to 500 µL of 13% Hb solution, which was prepared as described in Example 2. 500 µL of the PAL/Hb mixture were then dispersed in the ethyl cellulose solution using a probe sonicator. The water-in-oil emulsion was then spray dried under constant stirring using the conditions listed in Table 3. Product yield was determined by weighing the microcapsules in the collection vial of the spray dryer and dividing that value by the mass of the total solid content added in the water-in-oil emulsion. The product yield was determined to be about 70% with high reproducibility. Microcapsule size was determined by optical microscopy with a stage micrometer. PAL/Hb microcapsule size was 3.7±1.1 µm (mean±S.D., n=40).

TABLE 3

Spray drying conditions for the preparation of PAL microcapsules

| Polymer | Ethyl cellulose (100 cps) |
|---|---|
| Pump rate | 25% |
| Inlet temperature | 40° C. |
| Outlet temperature | 30° C. |
| Aspirator | 100% |
| Vacuum | −100 mbar |
| Feed concentration | 4% w/v |

Example 5: Analysis of PAL Activity in the Intact Microcapsules 100 mg of the spray dried PAL/Hb microcapsules were dispersed in 1500 µL of a 1% Tween 20 solution prepared using Tris buffer pH 8.5 as the solvent. 0.5 mL of 16 mM L-Phe solution was added to the microcapsule solution to yield a final L-Phe concentration of 4 mM. The solution was incubated at 37° C. for 7 minutes, and the reaction was stopped by adding 200 µL of the reaction mixture to 600 µL of trichloroacetic acid (10% w/v). The mixture was transferred into a 'frosted' 1 mL Duall tissue grinder, and the microcapsules were broken using 10 dounce strokes. The mixture was vortexed for 30 seconds and centrifuged at 8800 rpm for a period of 10 minutes, after which the supernatant was collected. The supernatant was analyzed by HPLC using the parameters as described elsewhere herein and evaluated through comparison with standardized solutions.

Example 6: Determination of Functional Efficiency

A 6 µL aliquot of glycerol free PAL was diluted to 1500 µL using a 1% Tween 20 solution in Tris buffer pH 8.5. 0.5 mL of 16 mM L-PA was added to yield a final concentration of 4 mM. The reaction mixture was incubated at 37° C. for 7 minutes while stirring. The reaction was stopped by adding 200 µL of the reaction mixture to 600 µL of (10% w/v) trichloroacetic acid solution. The mixture was vortexed and analyzed for trans-cinnamic acid content by HPLC using previously described parameters. The functional efficiency was computed using the data collected in Examples 5-6 and the following formula:

$$\text{Functional Efficieny} = \frac{\text{Activity of the total amount of microcapsules recovered}}{\text{Activity of the initial amount of }PAL\text{ added to manufacture the microcapsules}}$$

The mean functional efficiency of the PAL microcapsules was 28.2±2.5% (mean±S.D., n=3).

Example 7: Determination of Encapsulation Efficiency of the Microcapsules

Encapsulation efficiency of total protein (hemoglobin and PAL) in the microcapsules was determined using a modified Bradford's assay procedure. Briefly, 10 mg of PAL/Hb microcapsules were dissolved using 5 mL DCM. Following dissolution, the DCM was evaporated under nitrogen. The residue was dissolved in a 1 mL re-solubilizing agent containing 8 M Urea and 5% 2-mercaptoethanol. A 50 µL aliquot of the re-solubilized solution was diluted to 800 µL with nano-pure water and then incubated with 200 µL of the Bradford's reagent. The absorbance of the solution was read at 595 nm. All hemoglobin standards were processed similar to the samples. The amount of protein in 10 mg of microcapsules was used to compute the total amount of encapsulated proteins in the entire batch of recovered microcapsules and the following formula was used:

$$\text{Encapsulation Efficiency} = \frac{\text{Total amount of proteins in the recovered microcapsules}}{\text{Initial amount of }PAL + Hb\text{ in the aqueous phase}}$$

The mean encapsulation efficiency of the microcapsules was 12.6±1.8% (mean±S.D., n=3).

Example 8

PAL activity was markedly decreased over a 120 minute incubation at 37° C. in 0.1 M Tris buffer pH 8.5 (Table 4).

TABLE 4

Product formation measured over 7 and over 120 minutes

| Time [minutes] | Activity [µM/(min * µg protein)] |
|---|---|
| 7 | 0.73 |
| 120 | 0.36 |

Figure 4:
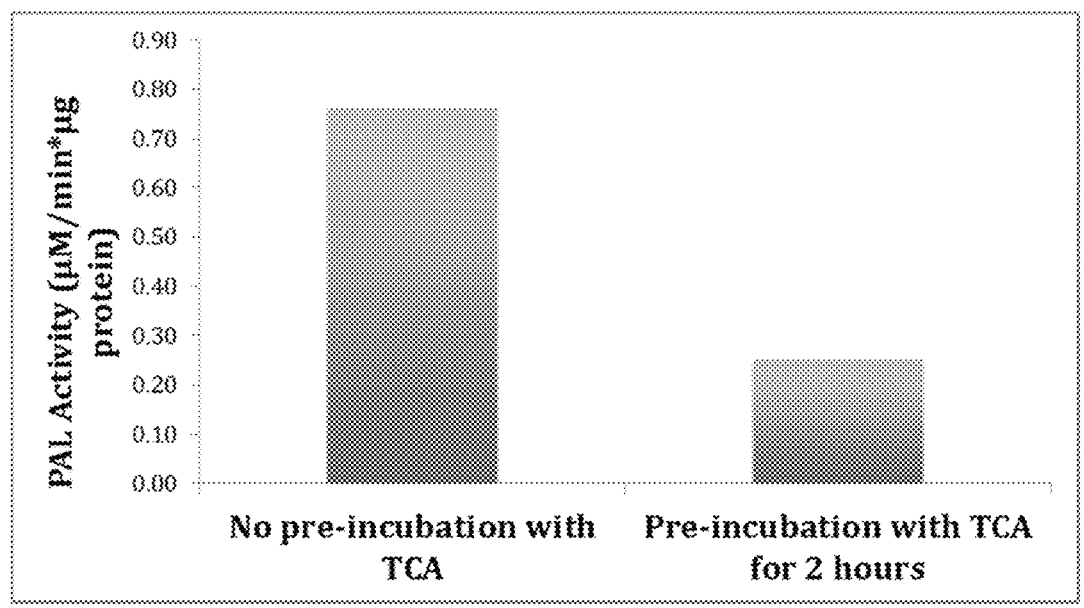
FIG. 4 is a bar graph illustrating certain effects of pre-incubation with trans-cinnamic acid on the activity of PAL.

Subsequent experiments showed that the decrease in PAL activity was not due to substrate depletion or enzyme denaturation during the 120 minute incubation at 37° C. Instead, determination of enzyme activity after a 120 minute pre-incubation with the reaction product, namely trans-cinnamic acid, showed that the decrease in PAL activity was due to inhibition of the enzyme by trans-cinnamic acid (FIG. 4).

PAL activity was then determined in the presence of fatty acid-free albumin (10% w/v), which interacts with trans-cinnamic acid and can sequester that reaction product, thus relieving product inhibition of PAL. In certain embodiments, trans-cinnamic acid binds more tightly to fatty acid-free albumin than fatty acid-containing albumin. In fact, the use of fatty acid-free albumin prevented PAL inhibition of PAL by trans-cinnamic acid over a 120 minute incubation (FIG. 5). The maximum activity of PAL (measured over 7 mins) in 10% fatty acid-free albumin solution was slightly (about 15%) lower than in pH 8.5 Tris buffer possibly due to steric hindrance of substrate-enzyme interaction or due to modest binding of the substrate by albumin, and the consequent decrease in free substrate for the enzymatic reaction.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A pharmaceutical composition comprising a microcapsule, which is enveloped by a membrane comprising ethyl cellulose, and wherein the microcapsule comprises in its interior phenylalanine ammonia lyase and fatty acid-free albumin, wherein the microcapsule has a diameter ranging from about 1 µm to about 10 µm.

2. The composition of claim 1, wherein the microcapsule further comprises in its interior a carrier compound.

3. The composition of claim 2, wherein the carrier compound is at least one selected from the group consisting of polyvinylalcohol, polysorbate 80, bovine serum albumin, a magnesium salt, a manganese salt, and glycerol.

4. The composition of claim 1, wherein L-phenylalanine flows freely across the membrane, and wherein a polypeptide with a molecular weight greater than about 20 kD cannot significantly cross the membrane.

5. The composition of claim 4, wherein the membrane is not chemically or physically degraded or digested within the gastrointestinal tract of a human.

6. The composition of claim 1, wherein the microcapsule has a diameter ranging from about 3 to about 5 µm.

7. A method of preparing the composition of claim 1, the method comprising:
   a) contacting ethyl cellulose with dichloromethane to form an organic phase;
   b) contacting phenylalanine ammonia lyase, fatty acid-free albumin, buffered water solution, and optionally a carrier compound, thus forming an aqueous phase;
   c) contacting the aqueous phase with the organic phase to form a system;
   d) sonicating the system to form an emulsion;
   e) spray drying the emulsion to yield the composition.

8. The method of claim 7, wherein the organic phase comprises about 2-6% (w/v) ethyl cellulose.

9. The method of claim 7, wherein the aqueous phase comprises about 5-15% (w/v) of fatty acid-free albumin.

10. The method of claim 7, wherein the aqueous phase comprises about 5-15% (w/v) phenylalanine ammonia lyase.

11. A method of treating phenylketonuria in a subject in need thereof, the method comprising administering to the subject a therapeutically effective amount of the composition of claim 1.

12. The method of claim 11, wherein the microcapsule further comprises in its interior a carrier compound.

13. The method of claim 12, wherein the carrier compound is one or more selected from the group consisting of polyvinylalcohol, polysorbate 80, bovine serum albumin, magnesium, manganese and glycerol.

14. The method of claim 11, wherein L-phenylalanine flows freely across the membrane, and wherein a polypeptide with a molecular weight greater than about 20 kD cannot significantly cross the membrane.

15. The method of claim 11, wherein the microcapsule has a diameter ranging from about 3 to about 5 μm.

16. The method of claim 11, wherein the composition is administered to the subject orally.

17. The method of claim 11, wherein the composition is administered at a time selected from before mealtime, during mealtime, and after mealtime.

18. The method of claim 11, wherein administration of the composition to the subject has at least one effect selected from the group consisting of: ameliorate or reduce phenylalanine levels in the blood of the subject; and treat or ameliorate at least one symptom of phenylketonuria in the subject.

19. The method of claim 18, wherein the at least one symptom is selected from the group consisting of seizures, tremors, shaking, stunted growth, hyperactivity, eczema, musty odor, mental deficits, behavioral disorders and skin discoloration.

* * * * *